(12) United States Patent
Krupa et al.

(10) Patent No.: US 9,055,863 B2
(45) Date of Patent: Jun. 16, 2015

(54) PORTABLE ENDOSCOPE

(75) Inventors: Robert J. Krupa, Leominster, MA (US); William F. Laflash, Northbridge, MA (US); Thomas V. Root, Beverly, MA (US); Aleksandra A. Levshina, Leominster, MA (US)

(73) Assignee: Optim, Inc., Sturbridge, MA (US)

( * ) Notice: Subject to any disclaimer, the term of this patent is extended or adjusted under 35 U.S.C. 154(b) by 2007 days.

(21) Appl. No.: 11/599,196

(22) Filed: Nov. 14, 2006

(65) Prior Publication Data

US 2008/0114207 A1    May 15, 2008

(51) Int. Cl.
*A61B 1/00* (2006.01)
*A61B 1/04* (2006.01)
*A61B 1/12* (2006.01)
*A61B 1/06* (2006.01)
*G01M 3/34* (2006.01)

(52) U.S. Cl.
CPC ......... *A61B 1/00142* (2013.01); *A61B 1/00068* (2013.01); *A61B 1/0684* (2013.01)

(58) Field of Classification Search
USPC ................. 600/131, 160, 130, 133, 101, 155, 600/178–180; 362/555; 73/49.3
See application file for complete search history.

(56) References Cited

U.S. PATENT DOCUMENTS

| | | |
|---|---|---|
| 3,111,230 A | 11/1963 | Pesenti |
| 3,299,731 A | 1/1967 | Russell |
| 3,365,975 A | 1/1968 | Hathaway |
| 3,394,611 A | 7/1968 | Beurrier |
| 3,938,402 A | 2/1976 | Citrin |
| 3,963,438 A | 6/1976 | Banez |
| 3,986,498 A | 10/1976 | Lewis |
| 4,101,197 A | 7/1978 | Kent et al. |
| 4,212,021 A | 7/1980 | Ono et al. |
| 4,385,344 A | 5/1983 | Gonser |
| 4,449,518 A | 5/1984 | Konomura |
| 4,534,208 A * | 8/1985 | Macin et al. .................. 73/49.3 |
| 4,617,915 A | 10/1986 | Arakawa |
| 4,739,128 A | 4/1988 | Grisham |
| 4,763,100 A | 8/1988 | Wood |
| 4,850,716 A | 7/1989 | Baker et al. |
| 4,862,872 A | 9/1989 | Yabe et al. |
| 4,919,113 A | 4/1990 | Sakamoto et al. |
| 4,974,607 A | 12/1990 | Miwa |
| 4,998,926 A * | 3/1991 | Alchas .......................... 604/251 |
| 5,050,449 A | 9/1991 | Falcou et al. |
| D330,020 S | 10/1992 | Jung |
| D333,601 S | 3/1993 | Wingert |
| 5,217,003 A | 6/1993 | Wilk |
| 5,238,025 A | 8/1993 | Preston |
| 5,290,279 A * | 3/1994 | Bonati et al. .................. 606/15 |

(Continued)

FOREIGN PATENT DOCUMENTS

DE    202 11713    11/2002
JP    5264871    10/1993

(Continued)

*Primary Examiner* — Ryan Henderson
(74) *Attorney, Agent, or Firm* — Burns & Levinson LLP (57) ABSTRACT

Provided herein are water-tight, portable endoscopes that include the light and power source incorporated into a sealed compartment (also referred to herein as sealed canister) within the endoscope handle. The description also features water-tight, endoscope handles that include the light and power source incorporated into a sealed canister within the handle. In some embodiments, the sealed compartment contains all of the electronic components of the endoscope.

4 Claims, 13 Drawing Sheets

(56) References Cited

U.S. PATENT DOCUMENTS

| | | |
|---|---|---|
| 5,359,993 A | 11/1994 | Slater et al. |
| 5,368,015 A | 11/1994 | Wilk |
| 5,373,317 A | 12/1994 | Salvati et al. |
| 5,408,991 A | 4/1995 | Iida et al. |
| D358,471 S | 5/1995 | Cope et al. |
| 5,497,847 A | 3/1996 | Ota et al. |
| 5,535,141 A | 7/1996 | Lussi |
| 5,586,207 A | 12/1996 | Goodwin |
| 5,609,561 A | 3/1997 | Uehara |
| 5,634,711 A | 6/1997 | Kennedy et al. |
| 5,655,411 A | 8/1997 | Avitan et al. |
| 5,680,492 A | 10/1997 | Hopler et al. |
| 5,732,401 A | 3/1998 | Conway |
| 5,830,121 A | 11/1998 | Enomoto et al. |
| 5,846,183 A | 12/1998 | Chilcoat |
| 5,920,054 A | 7/1999 | Uber, III |
| 5,984,875 A | 11/1999 | Brune |
| 6,059,718 A | 5/2000 | Taniguchi et al. |
| 6,092,722 A | 7/2000 | Heinrichs et al. |
| 6,092,935 A | 7/2000 | Althaus et al. |
| 6,193,510 B1 | 2/2001 | Tsimerman |
| 6,240,312 B1 | 5/2001 | Alfano et al. |
| 6,260,994 B1 | 7/2001 | Matsumoto et al. |
| 6,318,887 B1 | 11/2001 | Matsumoto |
| 6,331,156 B1 | 12/2001 | Haefele et al. |
| 6,366,206 B1 | 4/2002 | Ishikawa et al. |
| 6,436,032 B2 | 8/2002 | Eto et al. |
| 6,438,302 B1 | 8/2002 | Utsui et al. |
| 6,452,624 B1 | 9/2002 | Aloy |
| 6,461,295 B2 | 10/2002 | Takada |
| 6,485,684 B1 | 11/2002 | Mapson et al. |
| D466,773 S | 12/2002 | Lin |
| 6,679,835 B2 | 1/2004 | Moriyama |
| 6,712,756 B1 | 3/2004 | Kura et al. |
| 6,712,760 B2 | 3/2004 | Sano et al. |
| 6,726,620 B2 | 4/2004 | Shibata et al. |
| 6,776,537 B2 | 8/2004 | Toyama |
| 6,793,622 B2 | 9/2004 | Konomura et al. |
| 6,814,932 B2 | 11/2004 | Hlebovy et al. |
| 6,832,849 B2 | 12/2004 | Masumura et al. |
| 6,884,392 B2 | 4/2005 | Malkin et al. |
| 6,918,693 B2 | 7/2005 | Ota et al. |
| 6,921,920 B2 | 7/2005 | Kazakevich |
| 6,932,599 B1 | 8/2005 | Hartung |
| 2001/0033807 A1 | 10/2001 | Lin et al. |
| 2001/0041825 A1 | 11/2001 | Shibata et al. |
| 2001/0056224 A1 | 12/2001 | Renner et al. |
| 2002/0013510 A1 | 1/2002 | Moriyama |
| 2002/0120181 A1 | 8/2002 | Irion |
| 2002/0188173 A1 | 12/2002 | Kobayashi |
| 2003/0109837 A1 | 6/2003 | McBride-Sakal |
| 2003/0141507 A1 | 7/2003 | Krames et al. |
| 2003/0156430 A1 | 8/2003 | Oto et al. |
| 2003/0231843 A1 | 12/2003 | Columbo et al. |
| 2003/0235800 A1 | 12/2003 | Qadar |
| 2004/0004846 A1 | 1/2004 | Steen et al. |
| 2004/0024290 A1 | 2/2004 | Root et al. |
| 2004/0041031 A1 | 3/2004 | Root et al. |
| 2004/0049172 A1 | 3/2004 | Root et al. |
| 2004/0052679 A1 | 3/2004 | Root et al. |
| 2004/0059191 A1 | 3/2004 | Krupa et al. |
| 2004/0225190 A1 * | 11/2004 | Kimoto et al. ............... 600/177 |
| 2004/0246744 A1 | 12/2004 | Krupa et al. |
| 2005/0075539 A1 * | 4/2005 | Schulz et al. ............... 600/160 |

FOREIGN PATENT DOCUMENTS

| | | | | |
|---|---|---|---|---|
| JP | 5313045 | | 11/1993 | |
| JP | 8-317897 | | 12/1996 | |
| JP | 2002112953 A | * | 4/2002 | ............ A61B 1/00 |
| JP | 2003-135367 | | 5/2003 | |
| JP | 2003169777 A | * | 6/2003 | ............ A61B 1/00 |
| JP | 2004-129720 | | 4/2004 | |
| WO | 01/95228 | | 12/2001 | |
| WO | 02/071930 | | 9/2002 | |
| WO | 02/17171 | | 7/2003 | |
| WO | 2006/066022 | | 6/2006 | |

* cited by examiner

PORTABLE ENDOSCOPE

BACKGROUND

Endoscopes are commonly used to view a region inside a subject (e.g., a human, or animal), such as, for example, when performing a therapeutic or interventional medical procedure to view an interior area in the subject or to perform a medical or diagnostic procedure on an interior area of a subject. Typically, an endoscope has a manipulation portion (e.g., a handle) coupled to an elongated portion (e.g., a flexible elongated portion, a rigid elongated portion, a semi-rigid elongated portion). During use of the endoscope, the manipulation portion remains outside the subject while the elongated portion is at least partially disposed inside the subject. Generally, the elongated portion has one or more optical components (e.g., one or more lenses, fiber optics, video imager) to illuminate and view the region inside the subject, and the manipulation portion has one or more devices designed to control the optical components and the position of the elongated portion in the subject. In general, after each use in a medical procedure, the endoscope is cleaned to remove detritus, and subsequently disinfected and/or sterilized.

Regular use and cleaning of the endoscope can expose sensitive electronic components to liquids resulting in eventual failure of the device, yet frequent cleaning with liquid decontaminating agents is necessary. The cleaning process and diagnostic use expose the exterior of the endoscope to liquids that if allowed to contact the electronic components of the interior of the endoscope could cause the breakdown and/or malfunction of the electronic components. Routine use of the endoscope can result in permitting a cut, break, or other breach of the otherwise waterproof sheathing of the elongated portion of the endoscope permitting fluid to enter the interior of the elongated portion of the endoscope. Once inside, the fluid can migrate to and damage the electronic components of the endoscope.

Traditional light sources for endoscopic use are generally of two types: incandescent filament lamps and arc lamps. Both types of lamps are very inefficient in converting electrical power to light, and consequently produce large amounts of heat. The heat must be dissipated. Furthermore, these light sources typically reside outside of the endoscope itself. External light sources must be connected to the endoscope, thereby tethering the endoscope to the light source and limiting the portability and range of motion of the endoscope.

There have been numerous attempts to utilize low power (<1 W electrical power consumption, typically operating below 100 mW) LEDs coupled to fiber optic light guides as light sources for endoscopy, dentistry, and for remote illumination of objects. Most of these prior attempts employ numerous low power LEDs for remote illumination. Multiple LEDs have been necessary because the light output from a single, low power LED is very low and there is poor coupling of light emitted by the LED(s) into the optical fiber. In other examples, the LED light source is external to the endoscope and attached to the endoscope handle through a light guide post. This is problematic because there are very large light losses at the connection with the endoscope handle.

Thus, there is a need for a fully self-contained, portable endoscope that is not tethered to an external light and/or power source and that can withstand multiple uses and cleanings while maintaining the integrity of the liquid sensitive components of the endoscope.

SUMMARY OF THE INVENTION

The technology features an endoscope handle comprising a sealed compartment within the interior of the handle. In some embodiments, the sealed compartment comprises the electronic components of the endoscope. In some embodiments, the sealed compartment comprises a gas-permeable portion such that the sealed compartment is gas-permeable and liquid permeable.

As described herein, an endoscope handle is provided. In some embodiments, the endoscope handle comprises an exterior and an interior, a sealed compartment within the interior of the endoscope comprising an light emitting diode (LED), an LED power source, and a gas-permeable portion such that the sealed compartment is gas-permeable and liquid impermeable.

In some embodiments, the endoscope handle comprises an exterior and an interior, a valve, wherein the valve allows fluid communication between the exterior and the interior of the handle when the valve is open, a sealed compartment comprising an light emitting diode (LED), and an LED power source, wherein the sealed compartment is gas-permeable and liquid impermeable, and a magnetic power switch comprising a moveable magnetic source on the exterior of the handle and a magnetically activatable switch inside the sealed compartment.

Endoscopes are also provided. In some embodiments, the endoscope comprises the endoscope handle described herein and an elongated portion connected to the endoscope handle.

In some embodiments, the endoscope comprises a handle comprising an exterior and an interior and means for allowing fluid communication between the exterior and the interior of the handle. The endoscope further comprises a sealed compartment comprising means for generating light and means for allowing gas to enter the sealed compartment and for excluding liquid from entering the compartment. In some embodiments, the endoscope further comprises a means for activating the light generating means.

In some embodiments, the endoscope and endoscope handle include a light source, power source, light source drive electronics, and viewing optics within the handle of the endoscope. Everything needed for an examination can be contained within the endoscope. Thus, there is no need to connect the endoscope to an outside light and/or power source. In addition, as described herein, the electronics within the endoscope handle are in a separate compartment that is sealed from the rest of the endoscope handle. As a result, even if the endoscope shaft leaks (due to damage, cuts or tears in the waterproof sheathing) or if liquid otherwise enters the endoscope handle, the electronics, including the LED, are protected from the liquid.

As a result of the present invention, the entire interior of the endoscope (handle, shaft, and electronics compartment) can be pressurized, for example, when testing for leaks. The gas-permeable portion of the sealed compartment keeps liquid out of the sealed compartment while permitting gas to penetrate the sealed compartment. Therefore, when the interior of the endoscope is pressurized, the handle, elongated portion (also referred to herein as shaft), and the seal on the sealed compartment are tested for leaks simultaneously. In this manner, leaks in the electronics seals, such as the door to the sealed compartment, can also be detected.

Thus, the endoscope and endoscope handle described herein can be routinely and easily tested for leaks. For example, the endoscope can be tested after every use. By testing the endoscope and/or endoscope handle for leaks after every use, potential contamination and liquid intrusion can be detected early on before the endoscope is otherwise damaged by exposing the electronic components to liquid.

The various embodiments described herein can be complementary and can be combined or used in a manner understood by the skilled person in view of the teachings contained herein.

DETAILED DESCRIPTION OF THE INVENTION

In general, the invention relates to water-tight, portable endoscopes that include the light and power source incorporated into a sealed compartment (also referred to herein as sealed canister) within the endoscope handle. The invention also relates to water-tight, endoscope handles that include the light and power source incorporated into a sealed canister within the handle. In some embodiments, the sealed compartment contains all of the electronic components of the endoscope.

Figure 1:
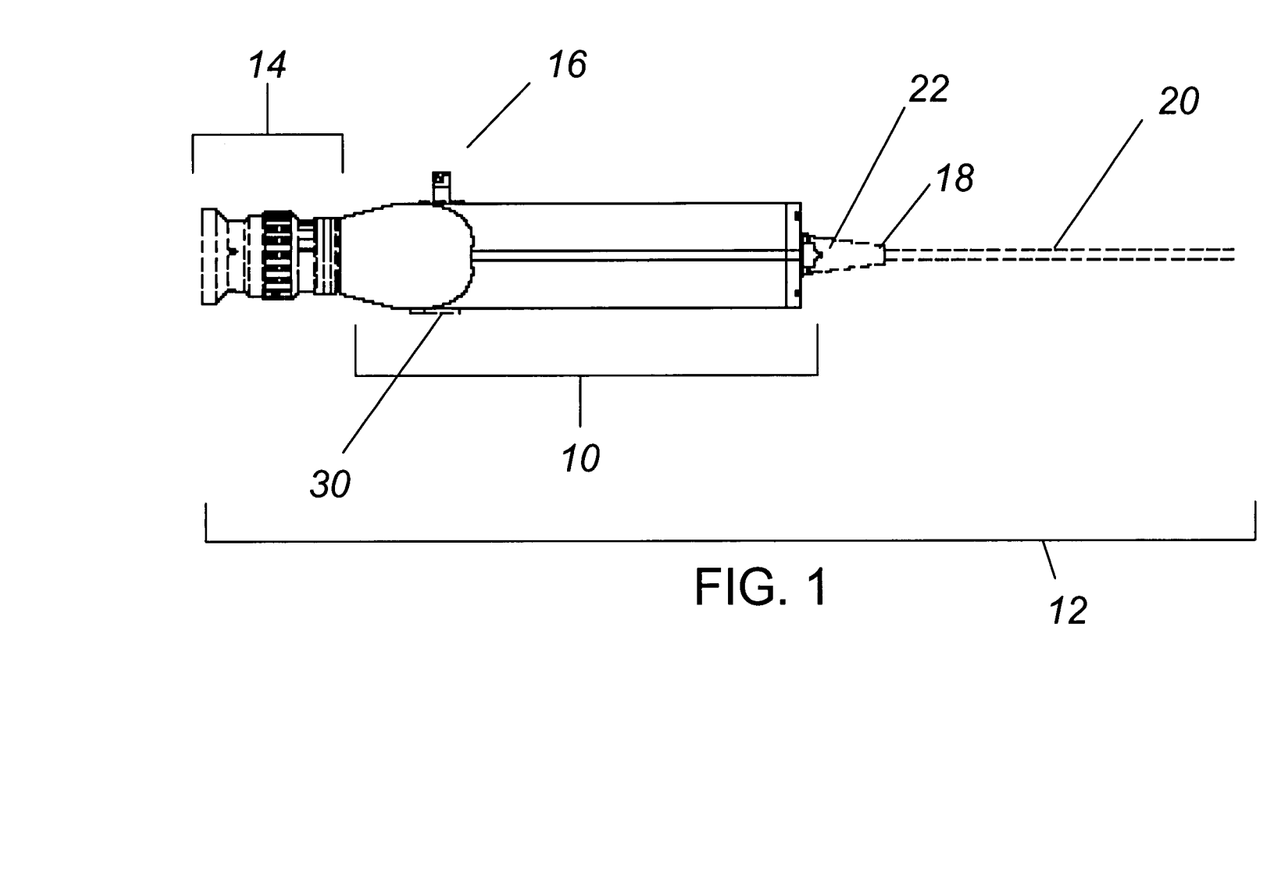
FIG. 1 shows a top view of an endoscope.

FIG. 1 is a top view showing an endoscope 12 and body of the endoscope handle 10. The body of the endoscope handle can be constructed from any material suitable for use in an endoscope handle that is or can be made waterproof. For example, the body of the endoscope handle can be constructed from plastic or metal or combinations thereof. In some embodiments, the body of the endoscope handle is aluminum.

As shown in FIG. 1, the endoscope handle can include an eyepiece 14, valve 16, power switch 22, and articulation lever 30. In some embodiments, a shaft 20, and a connector 18 are also employed. The valve 16 can be any suitable valve for sealing the interior of the handle from the exterior when the valve is closed and for allowing fluid communication between the exterior and interior of the handle. As used herein, fluid communication includes, for example, the entry and/or exit of gas. In some embodiments, the interior of the handle can be pressurized with bas when the value 16 is open. The valve 16 can also include a removable protective cap. The power switch 22 includes a suitable magnet or magnetic material and is configured to allow the user to move the switch such that the magnet or magnetic material is placed over a reed switch present in the interior of the endoscope handle, thereby tripping the reed switch and allowing power to flow from the power source to the light source. The power switch can be moved such that it is no longer placed over the reed switch, disengaging the reed switch and turning the endoscope OFF. In one embodiment, the power switch is attached asymmetrically on a post such that the power switch can be pivoted to place the magnet over the reed switch or to remove the magnet from the position over the reed switch.

The shaft 20 can be rigid or flexible. The shaft can be constructed from any suitable material used in the construction of endoscope shafts. The material can be waterproof or made to be waterproof. The shaft can be constructed as described, for example in U.S. Pat. No. 6,991,603 to Krupa et al. The shaft is connected to the handle (at the shaft connection opening 46 see FIG. 12B) via a suitable connector 18. The connector can include an O-ring, or other suitable material to create a water-tight seal around the shaft or light guide therein and the body of the handle. In some embodiments, a gasket is used to seal the joint between the shaft and the body of the handle.

Figure 2:
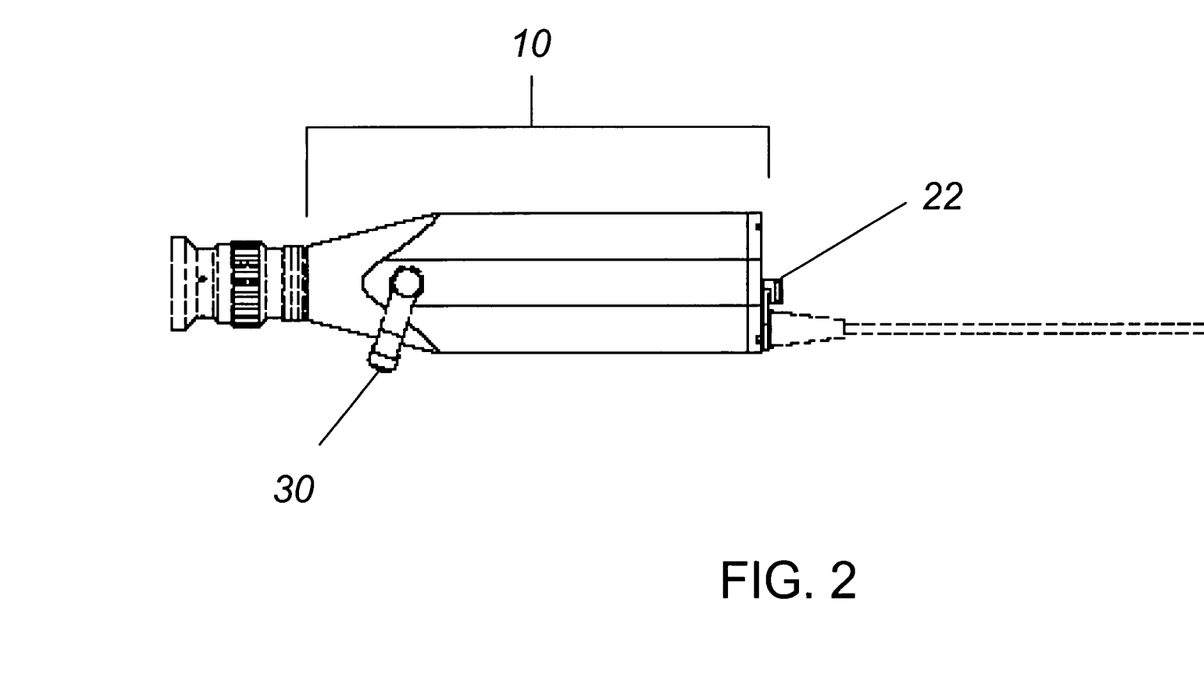
FIG. 2 is view of the right side an embodiment of endoscope.

FIG. 2 is view of the right side an embodiment of the present invention. In some embodiments, the shaft or elongated portion has an articulating distal end. The articulation of the distal end of the shaft can be controlled by the operator using the articulation control lever 30. In some embodiments, the distal end of the shaft can be articulated in two directions (e.g., up or down, "two-way articulation"). Methods for articulating the distal end of an endoscope shaft are described, for example, in US 2004/0059191 by Krupa, et al.

Figure 3A:
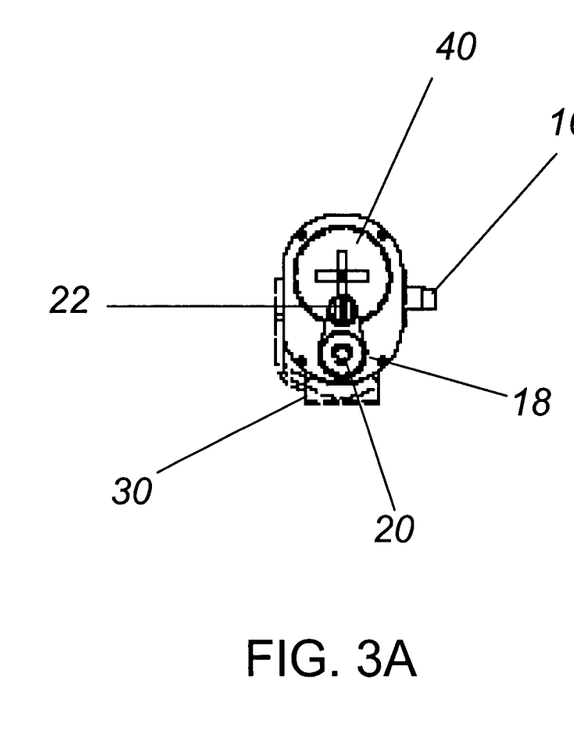
FIG. 3A is an end-on view of the front of an embodiment of endoscope.
Figure 3B:
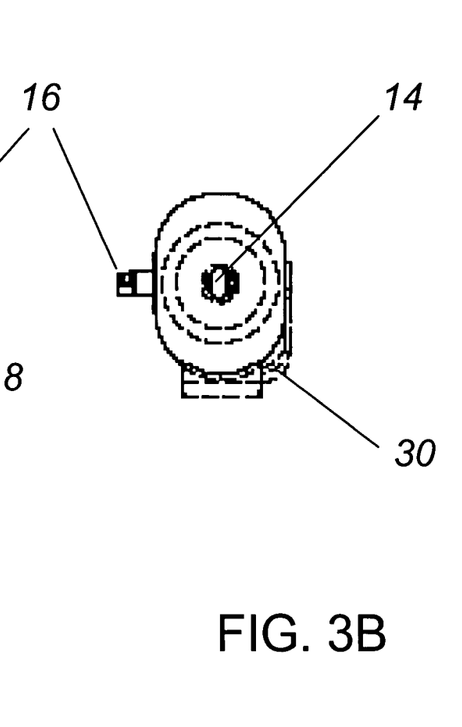
FIG. 3B is an end-on view of the rear of an embodiment of endoscope.
Figure 4:
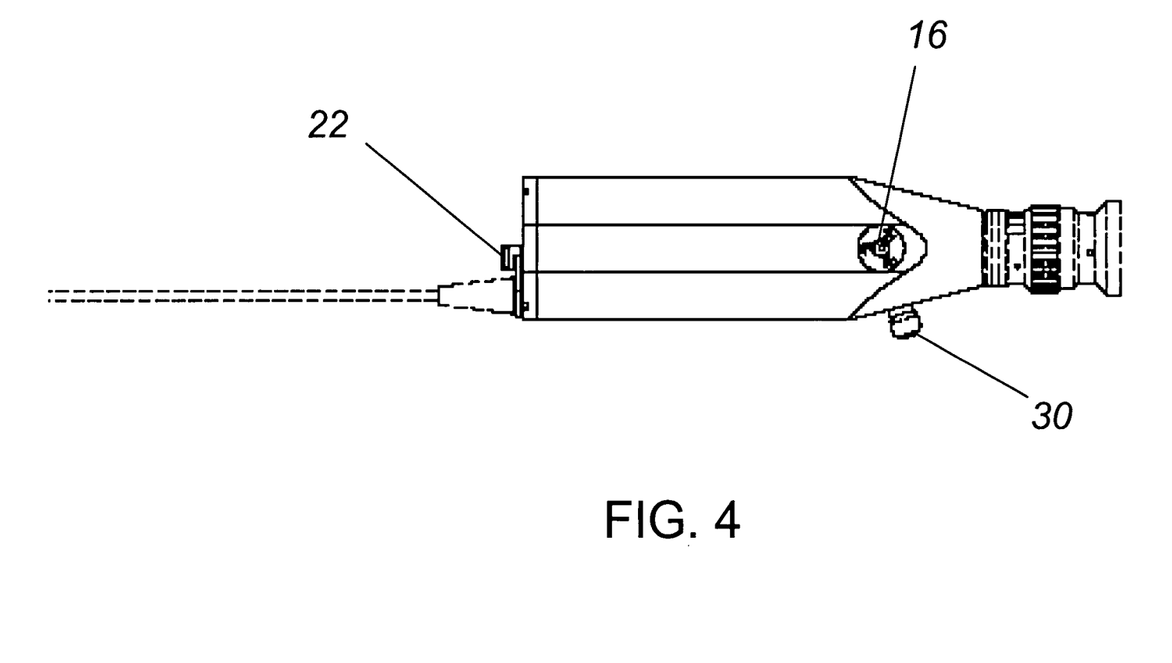
FIG. 4 is a view of the left side of an embodiment of endoscope.
Figure 5:
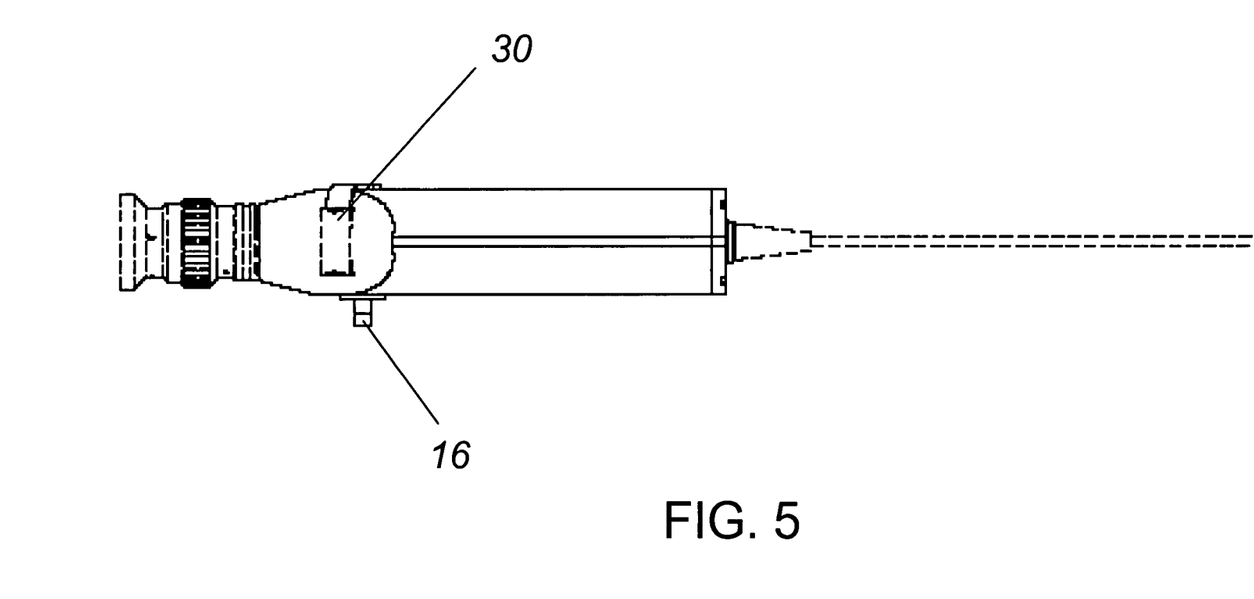
FIG. 5 is a bottom view of an embodiment of endoscope.
Figure 6:
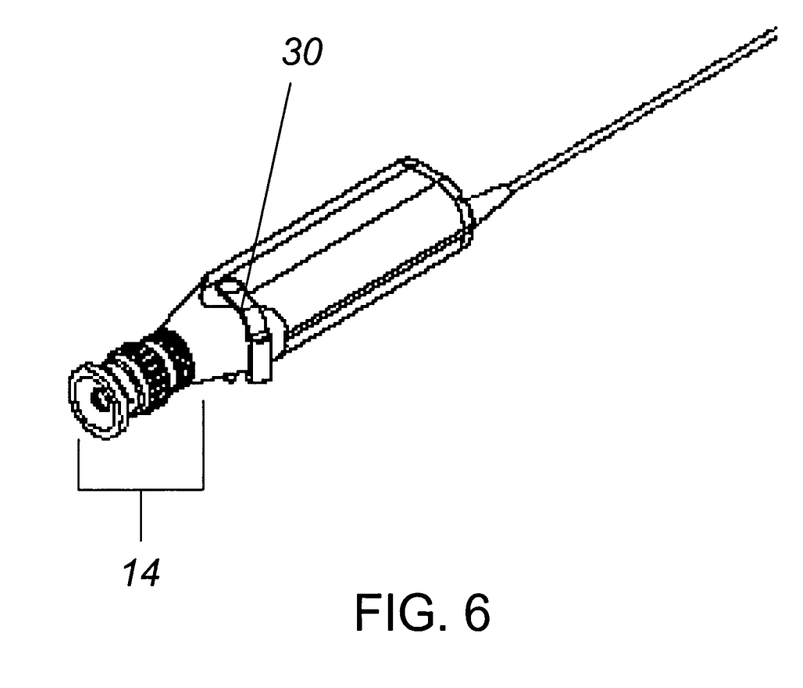
FIG. 6 shows a front elevation view of the right, bottom, and rear portions of an endoscope.
Figure 7:
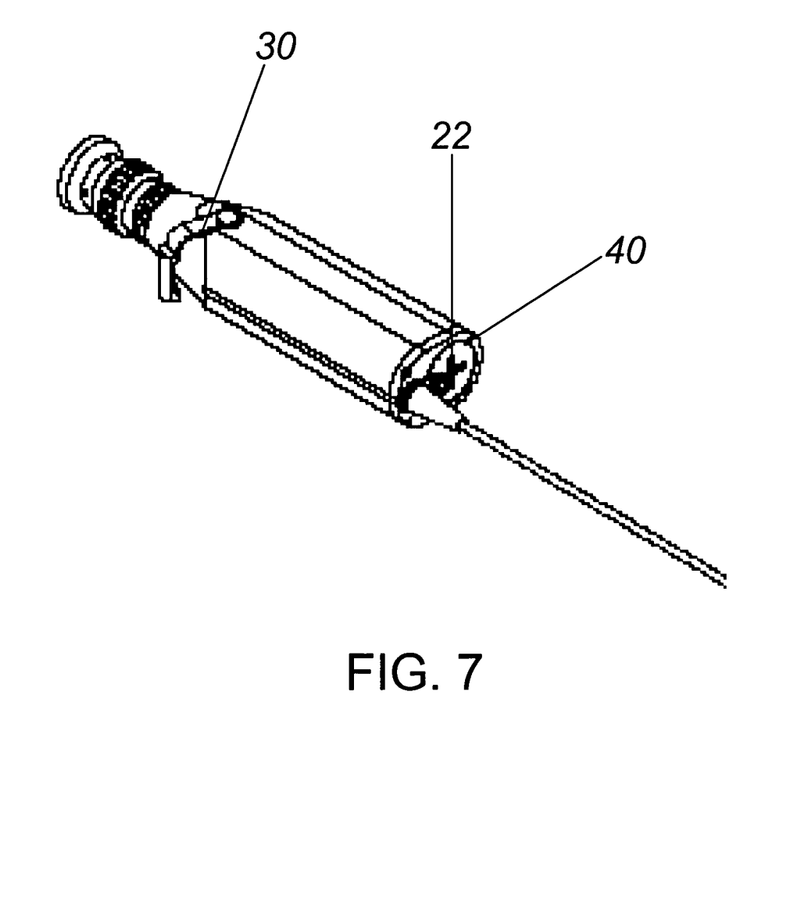
FIG. 7 shows a rear elevation view of the right, bottom, and front portions of an endoscope.
Figure 8:
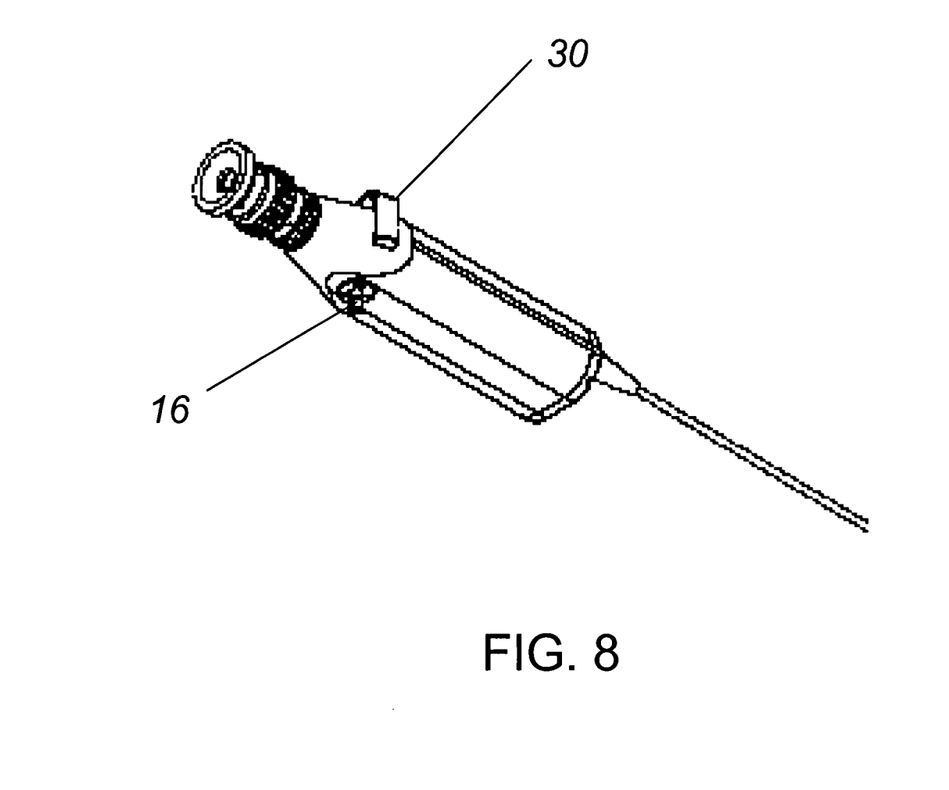
FIG. 8 shows a rear elevation view of the left, top, and rear portions of an endoscope.
Figure 9:
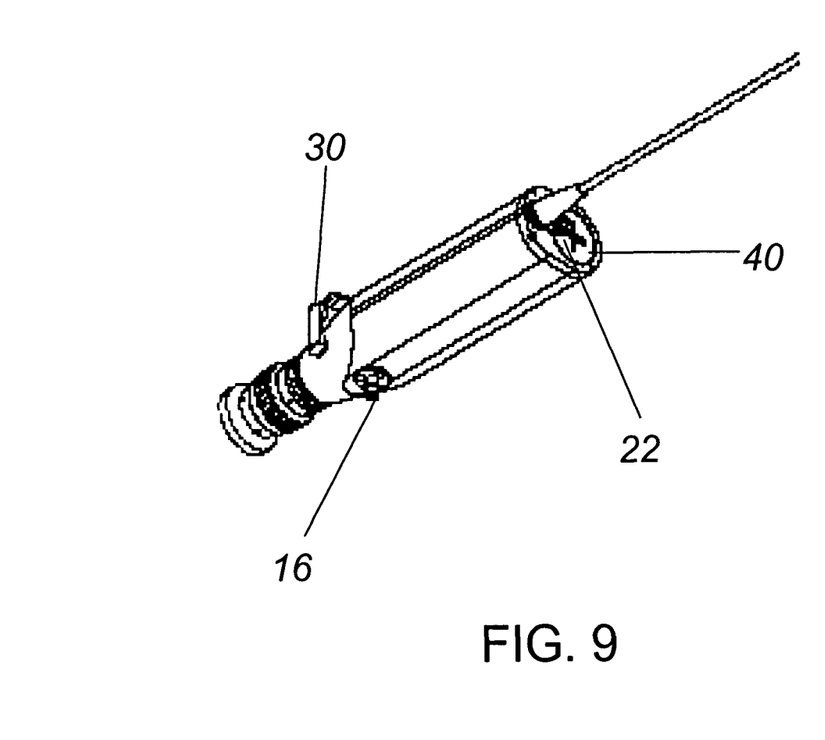
FIG. 9 shows a front elevation view of the left, top, and front portions of an endoscope.
Figure 10:
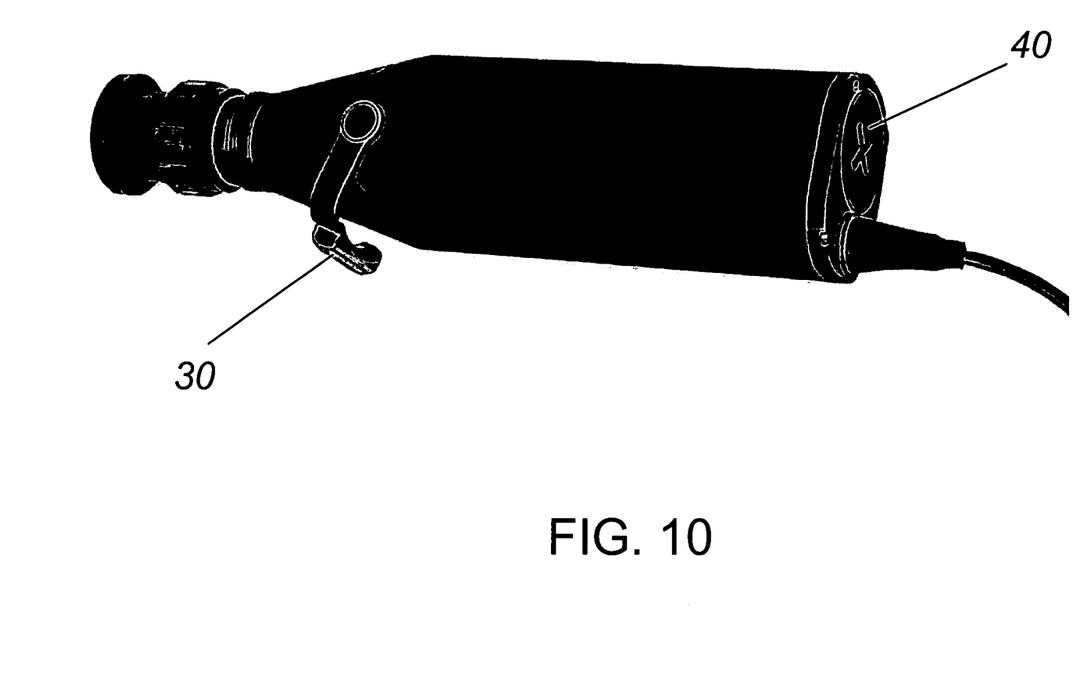
FIG. 10 shows the right and right bottom view of an endoscope.

FIG. 3A shows the front end of an embodiment of the present invention. As shown in FIG. 3A, the lever 22 is in the ON position. When in the ON position (e.g., straight up, or directly over the front of the door 40), the magnet trips a reed switch located inside of the sealed compartment and power flows from the power source to the light source. When in the OFF position (e.g., straight down, or such that it is not directly over the door 40), the reed switch is not tripped by the magnet and no power flows from the power source to the light source. Other switches can be used, for example a sealed push button switch can be used.

Door 40 allows access to the LED power source. The LED light source can be powered by small batteries that will operate for a considerable length of time without the need for battery replacement or recharging, and without making the endoscope handle cumbersome or unwieldy. However, if necessary, the batteries can be accessed and replaced through the door 40. The door can include groves to allow easy opening and removal of the door without the need for specialized tools. In some embodiments, the door can be opened with a coin. In some embodiments, the seal between the door and the handle is water-tight. A water-tight seal can be made for example, using a suitable sealing material such as an O-ring or a gasket. In other embodiments, the door can be a threaded plug. Any sealing mechanism that prevents liquids such as cleaning solution or other liquids from entering the handle.

FIGS. 3B and 4-10 show alternate views of an endoscope provided herein.

Figure 11:
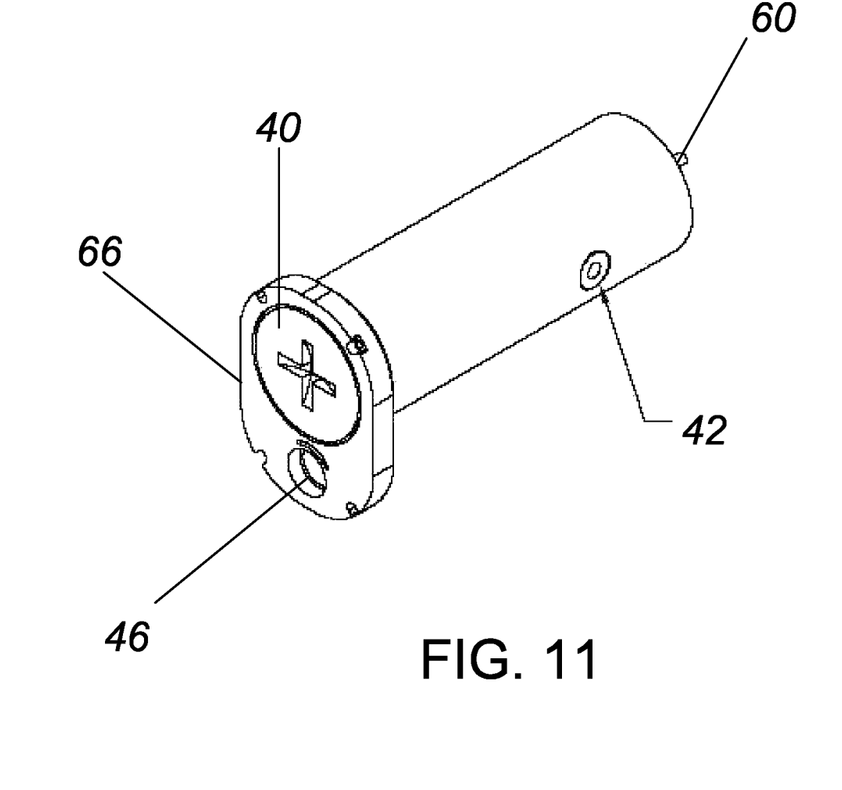
FIG. 11 shows an embodiment of a sealed compartment.

FIG. 11 shows an embodiment of a sealed compartment. The sealed compartment can be made of any suitable material for constructing a water-tight compartment, including metal, plastic, and combinations thereof. In some embodiments the material is light weight. The sealed compartment can be constructed, for example, from aluminum. The sealed compartment can include the front face plate 66, including the door 40 and a port 46 (shaft connection port) for connecting the elongated portion to the endoscope handle.

A gas-permeable portion 42 allows gas into and out of the sealed compartment and is impermeable to liquids such as water or cleaning solutions. In some embodiments, the gas-permeable portion comprises a gas-permeable membrane. The gas-permeable membrane can be, for example, polytetrafluoroethylene. Suitable gas-permeable membranes can be obtained from W. L. Gore (on the World Wide Web at gore.com). Suitable gas-permeable membranes include Quick Pressure Equalization vents from W. L. Gore. In some embodiments, the gas-permeable membrane is impermeable to liquids up to a pressure of about 10 PSI. The gas-permeable membrane can be in any suitable size or shape to form a gas-permeable portion of the sealed canister sufficient to let gas in during, for example, pressurized leak testing. Suitable forms of the membrane include a tape-like membrane or a membrane in a housing that screws into the sealed compartment. In some embodiments, the gas-permeable portion comprises a low profile gas-permeable membrane.

A portion of the light guide 60 is also shown. Shaft connection port 46 is where the elongated portion is connected to the face plate 66 of the sealed compartment.

Figure 12A:
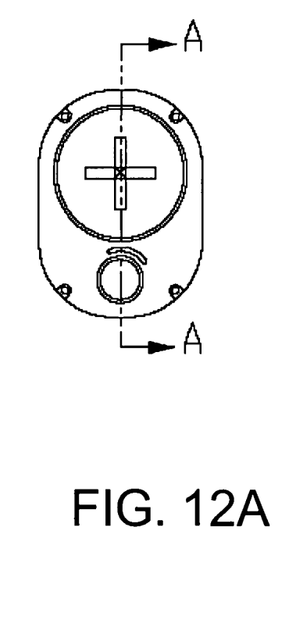
FIG. 12A shows a front-end view of a sealed compartment with cut-away view "A" marked.
Figure 12B:
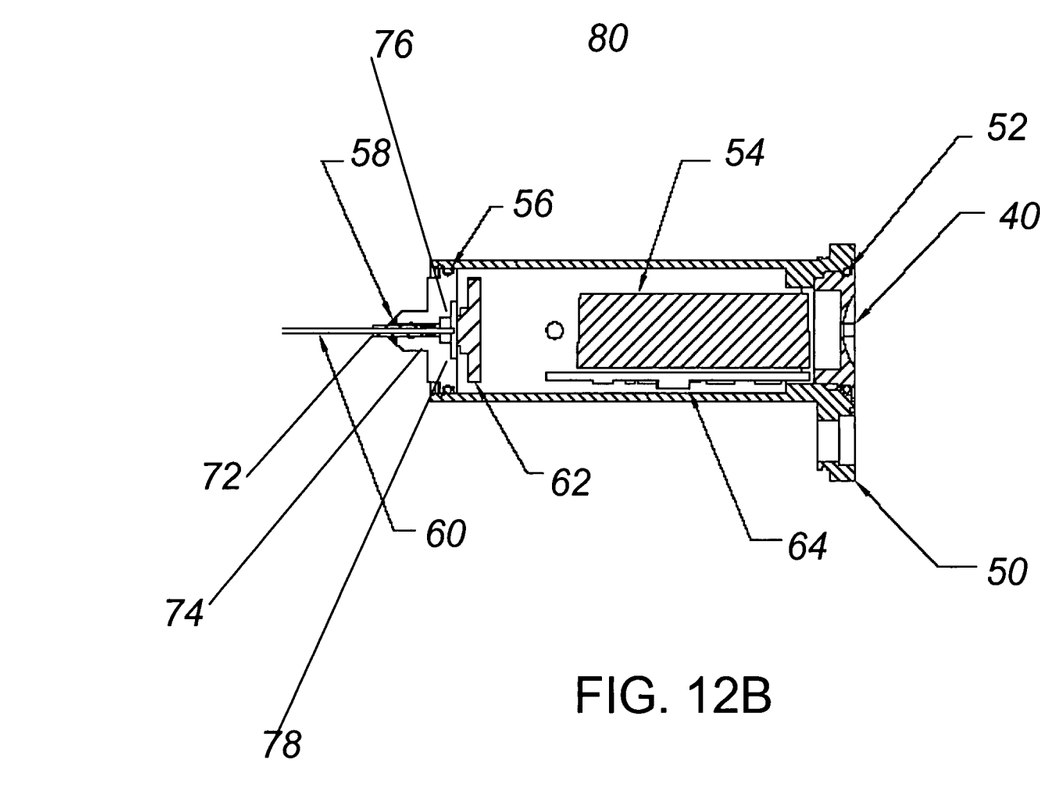
FIG. 12B shows the cut-away view "A" shown in FIG. 12A of the sealed compartment.

Shown in the cut-away view of FIG. 12B is the housing 50 for the sealed compartment, the door 40, and the light guide holder assembly 74. In some embodiments, the light guide holder is a solid piece made from a suitable material. The light guide holder is configured to hold the light guide in place against the light source 62. Suitable materials for the light guide holder include metals and plastics, so long as the material does not interfere with the ability of the light guide to gather and transmit light to the distal end of the shaft. In some embodiments, the light guide holder has hollowed out sections (76, 78) at the interface with the light source 62. In some embodiments, the hollowed out sections facilitate the alignment of the light guide with the light source 62.

The various junctions between the housing and other components of the sealed compartment are sealed with a material suitable to form a water-tight seal. Suitable seals include O-rings, gaskets, silicone seals, and adhesives such as silicone glue epoxy, room temperature vulcanizing (RTV) adhesives, and the like. In some embodiments, an O-ring 52 is used to form a seal between the door 40 and the housing 50. In some embodiments, an O-ring 56 is used to form a seal between the light guide holder 74 and the housing 50. In some embodiments, a silicone seal 58 is used to form a seal between the light guide 60 and the tip of the ferrule 72. It is understood that any suitable sealing agent for forming a water-tight seal can be used to seal the various junctions between the components of the sealed container and the various components and the housing.

Suitable light guides include one or more optical fibers. Optical fibers can be formed from a transparent material or any material which allows light to pass through. Examples of materials that can be used to form the light guide include glass, plastic, and sapphire. In addition, the light guide can be formed form a plurality of fibers (e.g., fiber bundle). In some embodiments a flexible light guide is used. FIG. 12B shows one embodiment where the light guide exits the sealed compartment from the left side of the figure (in the direction of the rear of the endoscope handle). The light guide then is curved around the sealed compartment such that the light guide exits the endoscope handle through the shaft connection port 46 (in the direction of the front of the endoscope).

The power source 54 and the electronics required for the power source 64 are enclosed within the sealed container 80. The electronic components include, for example, the light source, a source of power for the light source and any circuitry to provide the correct voltage to the light source. In some embodiments, the light source is a high power LED. The high power, very small size, and high efficiency of these devices makes it possible to design an untethered endoscope; an endoscope without a light guide umbilical connecting the endoscope to an external light source. Suitable batteries and circuitry to provide the correct voltage to a LED, including a high power LED, are well known in the art. In addition, in some embodiments, a magnetically activatable reed switch is present within the sealed compartment, as described supra.

In some embodiments, the light guide is a fiber optic and is closely coupled to a single high power LED. Close coupling the light guide to the LED, e.g., without the use of additional optical components, couples a large amount of the light emitted by the LED directly into the fiber or fibers of the light guide. As a result, a greater amount of light from the LED can be transmitted to the distal end of the endoscope shaft which illuminates objects under investigation. Some embodiments of the present invention do not include auxiliary optics, such as lenses or mirrors, disposed between the light source and the light guide bundle, but instead rely on the small size of the LED's emitting region and the close placement (e.g., direct contact or close proximity) of the light guide to the emitting region. Because the LED itself is very efficient in converting electrical energy into light and the described optical interface is very efficient at coupling this light from the LED into the light guide fiber, this LED light source can be powered by small batteries without making the endoscope handle cumbersome or unwieldy. The lack of auxiliary optics between the light source and the light guide simplifies the mechanical design and volume of space within the handle needed for the light source.

EXAMPLE

Leak Testing

After every procedure, the endoscope is tested to ensure that it is watertight. Testing is conducted prior to conducting high-level disinfection or sterilization.

The cap is first removed from valve 16 and a leak tester is attached to the valve. Suitable leak testers can be obtained, for example, from Surgical Repairs International (on the World Wide Web at srirepairs.com/products_leaktesters.asp). Using the leak tester, the interior of the endoscope is pressurized to about 140-180 mmHg as measured on the leak tester. The pressure measurement is observed for about 10 seconds to determine if the connection between the leak tester and the valve is loose. If the pressure drops, the connection between the endoscope and the leak tester may be loose. The attachment and pressurization procedure is repeated to verify.

If the pressure drops again, the endoscope may have a damaged seal and should not be immersed in any liquid. The endoscope should be repaired prior to using again or cleaning.

If the pressure does not drop the entire endoscope, while pressurized, is immersed in water. The endoscope is observed for 30 seconds. The distal end of the shaft is articulated up and down during this period; holes in the soft covering of the distal end of the shaft may not be evident in a relaxed position.

A steady stream of air bubbles indicates a leak in the endoscope. If a steady stream of bubbles is observed, the endoscope removed immediately from the water, while the endoscope is still pressurized. Air escaping the endoscope at the leak site will have prevented fluid invasion. If a leak is detected, the fiberscope should not be immersed in solution or used for patient procedures after the leak test.

Absence of a steady stream of air bubbles confirms that the endoscope is watertight. The endoscope is removed from the water and the leak tester is disconnected from the endoscope. The endoscope is then immersed in solution for cleaning and disinfection.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

We claim:

1. An endoscope, comprising:
   a handle formed of a housing having a sealed interior;
   a sealed container which houses a light emitting diode (LED), an LED power source, and a gas-permeable membrane, the sealed container being fully enclosed within the sealed interior and providing fluid communication with the sealed interior through the gas-permeable membrane, wherein the gas-permeable membrane is gas-permeable and liquid impermeable, thereby allowing gas to enter the sealed container during pressurized leak testing;
   a valve formed on the housing, wherein the valve allows fluid communication between an environment external to the housing and the sealed interior;
   a magnetic power switch comprising a moveable magnetic source on an exterior of the housing and a magnetically activatable switch inside the sealed container; and
   an elongated shaft extending from a distal end of the handle.

2. The endoscope of claim 1, wherein the gas-permeable membrane comprises polytetrafluoroethylene (PTFE).

3. The endoscope of claim 1, wherein the gas-permeable membrane is impermeable to liquid up to about 10 PSI.

4. The endoscope of claim 1, further comprising a door wherein the door allows access to the sealed container from the exterior of the housing when the door is in an open position.

* * * * *